United States Patent [19]
Rechelbacher et al.

[11] Patent Number: 6,090,375
[45] Date of Patent: *Jul. 18, 2000

[54] HAIR CONDITIONING SOLID

[75] Inventors: Horst M. Rechelbacher, Osceola, Wis.; Peter Matravers, Plymouth; Timothy R. Kapsner, Minneapolis, both of Minn.

[73] Assignee: AVEDA Corporation, Blaine, Minn.

[*] Notice: This patent is subject to a terminal disclaimer.

[21] Appl. No.: 09/120,110

[22] Filed: Jul. 21, 1998

Related U.S. Application Data

[63] Continuation of application No. 08/698,326, Aug. 6, 1996, Pat. No. 5,849,280.

[51] Int. Cl.[7] ................ A61K 7/06; A61K 7/11; A61K 7/075
[52] U.S. Cl. .............. 424/70.11; 424/70.1; 424/70.19
[58] Field of Search ................ 424/70.1, 70.11, 424/70.19

[56] References Cited

U.S. PATENT DOCUMENTS

| | | | |
|---|---|---|---|
| 4,668,508 | 5/1987 | Grollier et al. | 424/70.13 |
| 5,104,642 | 4/1992 | Wells et al. | 424/47 |
| 5,143,723 | 9/1992 | Calvo et al. | 424/63 |
| 5,209,924 | 5/1993 | Garbe et al. | 424/70.11 |
| 5,374,420 | 12/1994 | Gerstein | 424/70.11 |
| 5,849,280 | 12/1998 | Rechelbacher et al. | 424/70.11 |

*Primary Examiner*—Thurman K. Page
*Assistant Examiner*—Todd D Ware
*Attorney, Agent, or Firm*—Karen A. Lowney, Esq.

[57] ABSTRACT

The invention provides a cosmetic hair conditioning composition comprising: (a) an effective amount of a film forming polymer; and (b) a cosmetically acceptable vehicle, in which the composition is in the form of a solid. A cosmetic hair conditioning device and methods of conditioning and styling hair are also provided.

47 Claims, No Drawings

HAIR CONDITIONING SOLID

This application is a Continuation of Ser. No. 08/698,326, filed Aug. 6, 1996, now U.S. Pat. No. 5,849,280.

FIELD OF THE INVENTION

The present invention relates to cosmetic hair conditioning compositions in the form of solids, especially sticks. The invention also relates to a cosmetic hair conditioning device and methods of conditioning and styling hair.

BACKGROUND OF THE INVENTION

Human hair becomes soiled due to its contact with the surrounding atmosphere and, to a greater extent, from sebum secreted by the head. The build-up of the sebum causes the hair to have a dirty feel and an unattractive appearance. The soiling of the hair requires that it be shampooed frequently.

Shampooing the hair removes excess soil and sebum. However, the shampooing process has the disadvantage that the hair is left in a tangled and generally unmanageable state. A variety of approaches have been tried to alleviate this after-shampoo problem. These approaches range from the inclusion of hair conditioning aids in shampoos to post-shampoo application of hair conditioners, i.e., hair rinses. Difficulties associated with the use of conditioning aids in shampoos include compatibility problems and a greasy feel on the just-washed hair. Hair rinses typically work by depositing a polymeric film or other material onto the hair. However, the previous approaches to the after-shampoo problem have not been fully satisfactory. For one thing, hair rinses are generally liquid in nature and must be applied in a separate step following the shampooing, left on the hair for a length of time, and rinsed with fresh water. This process is time consuming and not convenient. The results obtained in this manner also have not been fully satisfactory due to the difficulties associated with the deposition and retention on the hair of the hair conditioning aid.

Conditioning and styling products ideally provide several benefits simultaneously. Desired benefits include conditioning, hold for styling, shine, etc. Existing conditioning and styling products are usually in the form of a spray, mousse, or gel. They usually contain a resin, such as an acrylate polymer or poly(vinylpyrrolidone/vinyl acetate) copolymer, which provides the hold, and other materials to modify the conditioning and other cosmetic benefits. They usually contain materials which plasticize the resin, reducing the flaking and making the hold less "crisp." When these products are applied to the hair, the volatile components such as water and alcohol evaporate, leaving the resin and other chemicals behind. If a plasticizer is used, it is usually at a very low level compared to the level of the resin. Too much plasticizer will significantly reduce the holding ability of the resin, make the product sticky, and create other undesirable aesthetic properties. Many different types of chemicals will plasticize a hair polymer, including glycerin, fragrances or other oils, silicones, and cosmetic esters.

A solid stick is used as the delivery form for many types of cosmetic products such as deodorants, lip conditioners, and color cosmetics. Stick formulas are generally based on either silicones, glycols and soap, or waxes. The glycol/soap base, which is water soluble or dispersible, is the traditional form for deodorants and antiperspirants. It consists primarily of water, glycols (such as glycerin or propylene glycol), alcohol and/or glycol esters, and is made into a solid form by addition of soap, usually sodium stearate.

The invention provides a cosmetic hair conditioning solid, especially in the form of a stick, that contains a hair styling polymer resin and results in a styling product that gives good hold to the hair, does not flake, and provides other cosmetic benefits, such as shine and conditioning. The bulk of the stick can be glycols, glycol esters, or other materials. In a traditional styling product, when glycols or glycol esters are present, their weight percent of the composition must be kept low to avoid plasticizing the resin to the point where it would lose most of its hold. However, in a solid of the invention the glycols or glycol esters are present at much higher weight percents of the composition and the composition has good hold. This difference in the effect of glycols and glycol esters in the properties of the compositions of the invention and their effect in traditional styling products emphasizes the different nature of the compositions of the invention.

The cosmetic hair conditioning solid of the present invention improves upon the prior art by providing a cosmetic hair conditioning composition that is in the form of a solid. The composition of the present invention is easy to use, both for conditioning and styling, and can be formed into any desired shape. The composition of the invention also requires a lesser amount of packaging than previous hair conditioners because it is more concentrated; the packaging constraints are also less stringent because it is a solid instead of a liquid or gel.

SUMMARY OF THE INVENTION

The invention provides a cosmetic hair conditioning composition comprising: (a) an effective amount of a film forming polymer; and (b) a cosmetically acceptable vehicle, in which the composition is in the form of a solid. The composition is preferably in the form of a stick.

The invention also provides a cosmetic hair conditioning device comprising: (a) a cosmetic hair conditioning composition; and (b) a holder for the cosmetic hair conditioning composition. The invention provides a method of conditioning hair comprising applying a cosmetic hair conditioning composition of the invention to hair.

Additional features and advantages of the invention are set forth in the description which follows and in part will be apparent from the description. The objectives and other advantages of the invention will be realized and attained by the cosmetic hair conditioning composition and cosmetic hair conditioning device and its uses as particularly pointed out in the written description and claims.

It is to be understood that both the foregoing general description and the following detailed description are exemplary and explanatory and are intended to provide further explanation of the invention as claimed.

DETAILED DESCRIPTION OF THE INVENTION

The invention provides a cosmetic hair conditioning composition comprising: (a) an effective amount of a film forming polymer; and (b) a cosmetically acceptable vehicle, in which the composition is in the form of a solid. The composition preferably has a hardness such that it will have a penetration measurement of not more than 200 in the Penetrometer Test. More preferably, the composition will have a penetration measurement of from 50 to 70 in the Penetrometer Test. The Penetrometer Test is performed with a standard penetrometer such as Model 73510 from Precision Scientific Petroleum Instruments Co. of Bellwood, Ill. A sample is prepared by pouring a sufficient amount of a melted composition of the invention into a glass jar about 6 cm in diameter to form a solid composition about 6 cm tall.

After the melted composition is cooled to room temperature to form a solid, the metal cone of the penetrometer is applied to the solid sample for 5 seconds with a load of 150 g. The penetration of the cone into the sample is measured in tenths of a millimeter to give a penetration measurement.

The cosmetic hair conditioning compositions preferably transfer an effective amount of a film forming polymer to hair when applied by hand. The cosmetic hair conditioning compositions of the invention are useful for styling and conditioning hair. When styling primarily is desired, it is often preferable to apply the cosmetic hair conditioning compositions of the invention to dry hair or hair that is slightly wet.

In a preferred embodiment the cosmetic hair conditioning composition is in the form of a stick; in another preferred embodiment the composition is in the form of a cylinder. The film forming polymer preferably is present in an amount of from 1 to 40 percent by weight, more preferably from 1 to 20 percent by weight, and most preferably from 3 to 15 percent by weight.

The film forming polymer can be a synthetic polymer or copolymer; the film forming polymer can be a naturally occurring polymer or copolymer. The composition can comprise at least one film forming polymer that is a synthetic polymer or copolymer and at least one film forming polymer that is a naturally occurring polymer or copolymer.

The film forming polymer can be a synthetic polymer or copolymer that is polymerized from an ethylenically unsaturated monomer or mixtures thereof. Preferred ethylenically unsaturated monomers include vinyl alcohol, vinyl acetate, vinyl propionate, N-vinyl acetamide, N-vinyl pyrrolidone, N-vinyl caprolactam, acrylic acid, methacrylic acid, $C_1$–$C_{12}$ esters of acrylic and methacrylic acid, acrylamide, methacrylamide, crotonic acid, vinyl neodecanoate, styrene, vinyl laurate, N-tertiary butyl acrylamide, methyl vinyl ether, ethylene, monobutyl maleate, maleic anhydride, allyl acetate, isobutyl vinyl ether, N,N-dimethylaminoethyl (meth) acrylate and its derivatives quaternized with dimethyl and diethyl sulfate, diallyl dimethyl ammonium chloride, vinyl substituted siloxanes or mixtures thereof.

Naturally occurring polymers or copolymers that can be used include cellulose, modified cellulose, carbohydrate polymer, or a modified carbohydrate polymer. Other naturally occurring polymers and copolymers that can be used include methyl cellulose, ethyl cellulose, hydroxyethyl cellulose, propylcellulose, hydroxypropylcellulose, carboxymethyl cellulose, chitosan, hydroxymethylcellulose, carboxyethyl cellulose, xanthan gum, alginic acid, quaternary nitrogen-containing cellulose ethers, graft copolymers of N,N-diallyl dimethyl ammonium chloride with cellulose, hydroxyethylcellulose and galactomannan gums, or quaternary chitosan derivatives, guar gum, locust bean gum, and modified forms thereof.

The film forming polymer can also be selected from vinyl acetate/vinyl pyrrolidone copolymer, vinyl alcohol/vinyl acetate copolymer, vinyl pyrrolidone/acrylamide copolymer, ethyl cellulose, vinyl acetate/crotonic acid copolymer, Eastman AQ sulfopolyester polymers, vinyl pyrrolidone/ethyl methacrylate copolymer, copolymer of dimethyl diallyl ammonium chloride and hydroxyethyl cellulose, hydroxypropyl cellulose, chitosan, vinylpyrrolidone/dimethylaminoethyl methacrylate copolymer, vinyl caprolactam/vinyl pyrrolidone copolymer, polyvinylpyrrolidone, polyacrylic acid, polyquaternium 4-copolymer of hydroxyethyl cellulose and diallyldimethyl ammonium chloride, poly(ethylhexyl methacrylate), poly-diallyldimethyl ammonium chloride, hydroxyethylcellulose, copolymer of vinylpyrrolidone/dimethylamino ethyl methacrylate quaternized with diethyl sulfate, polysilane 2-polymer formed by the reaction of tetradecene with polymerized tetramethyl cyclosiloxane, polyethylmethacrylate, or polyvinylacetate. In a preferred embodiment the film forming polymer is a vinyl acetate/vinyl pyrrolidone copolymer.

The cosmetically acceptable vehicle may be an aqueous or nonaqueous vehicle. In a preferred embodiment, the cosmetically acceptable vehicle comprises: (a) a fatty acid soap; (b) a nonionic component; and (c) water. In another embodiment, the cosmetically acceptable vehicle comprises: (a) a fatty acid soap; (b) a nonionic component; and (c) a lower alcohol.

A preferred composition of the invention comprises: (a) 1 to 15 weight percent of the film forming polymer; (b) 3 to 10 weight percent of a fatty acid soap; (c) 0 to 60 weight percent of a polyhydric alcohol; (d) 15 to 60 weight percent of a nonionic component; and (e) 10 to 50 weight percent of water, a lower alcohol, or mixtures thereof.

Another preferred composition comprises: (a) 3 to 10 weight percent of the film forming polymer; (b) 3 to 10 weight percent of a fatty acid soap; (c) 15 to 40 weight percent of a polyhydric alcohol; (d) 25 to 40 weight percent of a nonionic component; and (e) 20 to 45 weight percent of water, a lower alcohol, or mixtures thereof.

The compositions of the invention preferably comprise a sugar, more preferably table sugar. The sugar component provides additional stability to the stick. The compositions of the invention preferably comprise a polyhydric alcohol, more preferably a polyhydric alcohol selected from ethylene glycol, propylene glycol, or glycerol. The compositions of the invention preferably comprise a fatty acid soap, especially sodium stearate. In a preferred embodiment the compositions of the invention are transparent or translucent.

In a preferred embodiment the cosmetically acceptable vehicle comprises: (a) a polyhydric alcohol; (b) a $C_{14}$–$C_{18}$ sodium or potassium fatty acid soap; (c) a PEG-6 caprylic/capric triglyceride; (d) water; (e) a sugar; and (f) a $C_2$–$C_3$ monohydroxy alcohol. In another embodiment, the cosmetically acceptable vehicle is nonaqueous and comprises: (a) a polyhydric alcohol; (b) a $C_{14}$–$C_{18}$ sodium or potassium fatty acid soap; and (c) an alkoxylate copolymer. The alkoxylate copolymer preferably is a product having the formula

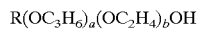

$$R(OC_3H_6)_a(OC_2H_4)_bOH$$

wherein R is selected from hydrogen or hydrocarbon chains having from 2 to 20 carbon atoms, a and b are each from 0 to 35 and the sum of a+b is from 5 to 35.

The invention provides a cosmetic hair conditioning composition comprising: (a) 5 to 30 weight percent water; (b) 0 to 60 weight percent of an aliphatic polyhydric alcohol having from 2 to 3 carbon atoms and from 2 to 3 hydroxyl groups; (c) 20 to 50 weight percent of a nonionic compound selected from $C_{12}$–$C_{18}$ alcohol alkoxylates, PEG (1–10) caprylic/capric triglycerides, or mixtures thereof; (d) 1 to 10 weight percent of a film forming polymer; (e) 3 to 7 weight percent of a sugar; (f) 3 to 10 weight percent of a fatty acid soap; and (g) 10 to 15 weight percent of an alcohol selected from ethanol, isopropyl alcohol or mixtures thereof; wherein the composition is in the form of a solid. This composition preferably is in the form of a stick. The polyhydric alcohol preferably is selected from ethylene glycol, propylene glycol, or glycerol. The nonionic material preferably is PEG-6 caprylic/capric triglyceride. The film forming polymer may be any of those described herein. The sugar preferably is table sugar and the fatty acid soap preferably is sodium stearate.

The invention provides a cosmetic hair conditioning composition comprising: (a) 20 to 30 weight percent of water; (b) 3 to 10 weight percent of sodium stearate; (c) 15 to 35 weight percent of PEG-6 caprylic/capric triglyceride; (d) 3 to 10 weight percent of a sugar; (e) 15 to 25 weight percent of glycerin; (f) 8 to 12 weight percent of vinylpyrrolidone/vinyl acetate copolymer; and (g) 8 to 15 weight percent of ethanol; wherein the composition is in the form of a solid stick.

The invention also provides a cosmetic hair conditioning composition comprising: (a) 25.6 weight percent water; (b) 7.0 weight percent sodium stearate; (c) 20.0 weight percent of PEG-6 caprylic/capric triglyceride; (d) 6.0 weight percent of table sugar; (e) 20.0 weight percent glycerin; (f) 10.0 weight percent of a vinyl acetate/vinyl pyrrolidone copolymer; (g) 10.0 weight percent ethanol; and the balance being other nonessential components.

The invention provides a cosmetic hair conditioning composition comprising: (a) 20 to 30 weight percent water; (b) 3 to 10 weight percent sodium stearate; (c) 25 to 40 weight percent PEG-6 caprylic/capric triglyceride; (d) 3 to 7 weight percent of a sugar; (e) 8 to 12 weight percent of a vinyl pyrrolidone/vinyl acetate copolymer; and (f) 8 to 15 weight percent of ethanol; wherein the composition is in the form of a solid stick.

The invention also provides a cosmetic hair conditioning composition comprising: (a) 26 weight percent water; (b) 7.0 weight percent sodium stearate; (c) 36.0 weight percent PEG-6 caprylic/capric triglyceride; (d) 6.1 weight percent table sugar; (e) 10.0 weight percent of a vinyl pyrrolidone/vinyl acetate copolymer; (f) 12.5 weight percent of ethanol; and the balance being other nonessential components.

The invention provides a cosmetic hair conditioning device comprising: (a) a cosmetic hair conditioning composition; and (b) a holder for the cosmetic hair conditioning composition; wherein the cosmetic hair conditioning composition comprises: (i) an effective amount of a film forming polymer; and (ii) a cosmetically acceptable vehicle; wherein the composition is in the form of a solid. The composition preferably transfers a cosmetically effective amount of a film forming polymer to hair when applied by hand. The composition preferably is in the form of a stick or cylinder. In a preferred embodiment the composition is in the form of a cylinder and the holder is in the form of a larger concentric cylinder. The holder preferably is made of plastic.

The invention provides a method of conditioning hair comprising applying a cosmetic hair conditioning composition to hair so that it is conditioned, wherein the cosmetic hair conditioning composition comprises: (i) an effective amount of a film forming polymer; and (ii) a cosmetically acceptable vehicle, in which the composition is in the form of a solid. The cosmetic hair conditioning composition preferably is applied by hand and preferably is applied to hair that is wet.

The invention also provides a method of styling hair comprising applying a cosmetic hair conditioning composition to hair so that it is styled, wherein the cosmetic hair conditioning composition comprises: (i) an effective amount of a film forming polymer; and (ii) a cosmetically acceptable vehicle, in which the composition is in the form of a solid. The cosmetic hair conditioning composition preferably is applied by hand and preferably is applied to hair that is dry or slightly wet.

The present invention provides a cosmetic formulation in stick form suitable for imparting aesthetic properties to the hair comprising: (a) an effective amount of a film forming polymer; and (b) a cosmetically acceptable vehicle suitable for forming the stick. The stick imparts shine, conditioning, and hold properties to the hair. The stick may be used to condition hair, preferable after shampooing but prior to completely drying.

The essential ingredients of the cosmetic hair conditioning composition of the present invention as well as optional components, the preparation of the compositions, and the use of the compositions are discussed in detail below.

An essential component of the present invention is the film forming polymer. A film forming polymer is a polymer that can be made to dissolve in a volatile vehicle such as water or alcohol and which, when the solvent evaporates, will deposit onto the hair to produce a thin layer with cosmetic/aesthetic benefits such as conditioning, hold, shine, etc. The film forming polymer is typically selected from synthetic polymers and copolymers, as well as naturally occurring polymers and copolymers as well as their chemically modified forms. The term polymer is used to refer to polymeric substances regardless of the number of types of -mer units in the substance. The term copolymer is used to refer to polymeric substances with two or more types of -mer units in the substance.

The synthetic polymers and copolymers and their chemically modified forms are derived from ethylenically unsaturated monomers selected from vinyl alcohol, vinyl acetate, vinyl propionate, N-vinyl acetamide, N-vinyl pyrrolidone, N-vinyl caprolactam, acrylic acid, methacrylic acid, $C_1$–$C_{12}$ esters of acrylic and methacrylic acid, acrylamide, methyacrylamide, crotonic acid, vinyl neodecanoate, styrene, vinyl laurate, N-tertiary butyl acrylamide, methyl vinyl ether, ethylene, monobutyl maleate, maleic anhydride, allyl acetate, isobutyl vinyl ether, N,N-dimethylaminoethyl (meth)acrylate and their derivatives quaternized with dimethyl and diethyl sulfate, diallyl dimethyl ammonium chloride, vinyl substituted siloxanes and mixtures thereof.

A preferred polymer is a copolymer of vinyl pyrrolidone and vinyl acetate having a molecular weight anywhere from 5,000 to 100,000. A suitable copolymer of vinyl pyrrolidone and vinyl acetate is available from BASF under the tradename Luviskol. Other polymers which can be used in the cosmetic sticks of the present invention include: a terpolymer of vinyl acetate, crotonic acid/vinyl neodecanoate sold under the names Resins 28, 29, and 30, available from National Starch; the sodium salt of polystyrene-sulphonic acid of molecular weight of about 500,000, sold under the name Flexan 500, available from National Starch; the sodium salt of a polystyrene-sulphonic acid of molecular weight of the order of 100,000, sold under the name Flexan 130, available from National Starch; a copolymer of N-tertiary butyl acrylamide, acrylamide, acrylic acid, and N-vinylpyrrolidone, sold under the name Quadramer 5, available from American Cyanamid; the monobutyl ester of a methyl vinyl ether/ maleic acid copolymer, sold under the name Gantrez ES 425, available from General Aniline; a copolymer of ethylene and monobutyl maleate sold under the name EMA 1325, available from Monsanto; a terpolymer of vinyl acetate, crotonic acid, and allyl dimethylpropanoate (77/8/15), a copolymer of vinyl acetate, crotonic acid, allyl dimethylpropanoate and vinyl laurate (77/8/14/1), a copolymer of vinyl acetate, allyl stearate and allyloxyacetic acid (80.5/15/4.5), a terpolymer of vinyl acetate, crotonic acid and polyethylene glycol, all available from Hoechst; a polymer of methacrylic acid, of molecular weight 10,000 and viscosity 1,000 cps, in the form of a 25% strength solution, available from Allied Colloids.

Additional useful film forming polymers include the following. A mixture of a homopolymer and a copolymer of acrylic acid, of molecular weight about 3,500, in the form of a 25% strength solution of viscosity 16 cps, available from Allied Colloids; a carboxyvinyl polymer, of high molecular weight, derived from acrylic acid, available from Goodrich Chemicals; a copolymer of allyl acetate and maleic anhydride, monoesterified with ethanol (50/50); a copolymer of isobutyl vinyl ether and maleic anhydride monoesterified with ethanol (50/50); a copolymer of allyl acetate and maleic anhydride amidified with docecylamine and dibutylamine (50/50); a terpolymer of allyl acetate, 2 ethyl hexyl acrylate and maleic anhydride, monoesterified with ethanol (47.4/2.6/50); and a copolymer of isobutyl vinyl ether, allyl neoheptanoate and maleic anhydride monoesterified with ethanol (18.2/31.8/50), all available from Hoechst.

The naturally occurring polymer, copolymers and their chemically modified forms preferably are selected from methyl cellulose, ethyl cellulose, hydroxyethyl cellulose, propylcellulose, hydroxypropylcellulose, carboxymethyl cellulose, chitosan, hydroxymethylcellulose, carboxyethyl cellulose, xanthan gum, alginic acid, quaternary nitrogen containing cellulose ethers, graft copolymers of N,N-diallyl dimethyl ammonium chloride with cellulose, hydroxyethylcellulose and galactomeannan gums and quaternary chitosan derivatives.

Other polymers such as a sulfonated polyester derived from sulphoisophthalic acid can also be used in the cosmetic compositions of the present invention. The film forming component preferably is present in the cosmetic compositions of the present invention at a level of from 1 to 15 weight percent and more preferably from 3 to 10 weight percent of the composition.

The cosmetic hair conditioning composition preferably includes a nonionic component. Preferred nonionic components of the present invention are $C_2$–$C_{20}$ alkanol alkoxylates and caprylic/capric polyol esters. A typical alkoxylate is an ethylene oxide and/or propylene oxide condensation product having the following formula:

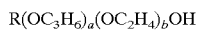

wherein R is either hydrogen or a hydrocarbon chain having from about 2 to 20 carbon atoms, preferably from about 4 to 18, a and b are each from 0 to 35 and a+b is from 5 to 35.

Examples of such products are a condensate of about 14 moles of propylene oxide with about one mole of butyl alcohol, available from Union Carbide under the name Fluid AP®; a polypropylene glycol having a molecular weight of 1200; a polyethylene glycol having a molecular weight of 420; a condensate of 20 moles of ethylene oxide and 5 moles of propylene oxide with one mole of cetyl alcohol; and a condensate of 15 moles of propylene oxide with one mole of stearyl alcohol. The preferred condensate is Fluid AP®.

The caprylic/capric polyol ester preferably is selected from caprylic/capric/diglyceryl succinate, caprylic/capric glycerides, caprylic/capric/lauric triglyceride, caprylic/capric/myristic/stearic triglyceride, caprylic/capric/stearic triglyceride, caprylic/capric triglyceride, caprylic/capric triglyceride PEG-4 esters and caprylic/capric triglyceride PEG-6 esters.

Other nonionic components which can be used in the compositions of the present invention include $C_{10}$–$C_{22}$ fatty alcohols such as lauryl alcohol, myristyl alcohol, stearyl alcohol, palmityl alcohol, behenyl alcohols and cetyl alcohols as well as their $C_1$–$C_4$ alkylene oxide adducts. Additional materials include PPG-3 myristyl ether and PPG-10 myristyl ether and their equivalents.

The nonionic component preferably is present in the compositions of the present invention at a level of from 20 to 50 weight percent, more preferably from 25 to 40 weight percent of the composition.

The cosmetic compositions of the present invention preferably include a sugar component. The sugar component of the present invention is typically a monosaccharide or a disaccharide. Typical monosaccharides are selected from glucose, fructose, mannose, or galactose. The disaccharide component is typically selected from sucrose, maltose, or lactose. A preferred sugar is table sugar. The sugar component preferably is present in the cosmetic compositions of the present invention at a level of from 2 to 10 weight percent, more preferably from 3 to 7 weight percent of the composition.

The cosmetic compositions of the present invention preferably include water. The water component of the present invention is typically deionized water, however, fresh tap water, spring water and distilled water can be used. The water content of the compositions of the present invention preferably is 10 to 30 weight percent, more preferably 20 to 30 weight percent of the composition. However, compositions of the invention may also be formed without water.

Another preferred component of the present cosmetic compositions is a polyhydric aliphatic alcohol containing 2 or 3 carbon atoms and from 2 to 3 hydroxyl groups. The polyhydric aliphatic alcohol component of the composition comprises from 0 to 60 weight percent, more preferably from 15 to 40 weight percent of the composition.

Suitable polyhydric alcohols for use in the gel compositions herein include ethylene glycol, propylene glycol, trimethylene glycol, and glycerine.

Another important component of the cosmetic compositions of the invention is a gel forming agent. The preferred gel forming agents are the sodium or potassium salts (i.e., soaps) of fatty acids containing from about 14 to 18 carbon atoms.

Soaps preferably comprise from 3 to 10 weight percent, more preferably from 4 to 8 weight percent of the composition. If soap concentrations lower than those specified are employed, the gels formed tend to be dimensionally unstable and tend to deform at summertime temperatures. If concentrations of soap above those specified are utilized, the gels formed tend to be too hard and do not exhibit desirable glide and application characteristics.

The fatty acid portion of the soap gel forming agents preferably are essentially pure saturated or unsaturated higher fatty acids having a $C_{14}$ to $C_{18}$ backbone. Suitable mixtures of such acids can be employed provided that such mixtures are free from significant proportions of other fatty acids of higher or lower chain length which substantially adversely affect or neutralize the desired gel forming effects.

Examples of fatty acids useful in synthesizing the gel forming agents herein include myristic, palmitic, stearic, oleic, linoleic, linolenic, margaric and mixtures of such acids. Naturally occurring sources of such fatty acids include coconut oil, beef tallow, lanolin, fish oil, beeswax, palm oil, peanut oil, olive oil, cottonseed oil, soybean oil, corn oil, rapeseed oil, rosin acids, and greases. Conventional fractionation and/or hydrolysis techniques can be employed if necessary to obtain the requisite types of fatty acids from such materials. Preferred fatty acid soap type gel forming agents include sodium stearate, sodium palmitate, potassium stearate, potassium palmitate and sodium myristate. The most preferred gel forming agent is sodium stearate.

The cosmetic compositions of the present invention preferably include from 8 to 15 weight percent and more preferably from 10 to 12 weight percent of a lower alcohol, preferably selected from ethanol, isopropanol, or mixtures thereof. A preferred embodiment has a 50:50 mixture of ethanol and isopropyl alcohol.

If the composition is nonaqueous, a silicone component is preferred. Typical silicones which can be used in the compositions of the present invention include nonvolatile and volatile silicones. The preferred silicones are selected from cyclomethicone, dimethicone, and polydimethylsiloxanes having 4, 5, and 6 silicon atoms consisting of between 30–40% $D_4$, 60–70% $D_5$, and 1–5% $D_6$ (Dow Corning Corporation $DC_{345}$ fluid). The silicone component preferably is present in the cosmetic stick of the present invention at a level of from 20 to 60 weight percent and more preferably from 25 to 55 weight percent of the composition when the vehicle is a nonaqueous vehicle.

The cosmetic compositions of the present invention can also include a preservative. Typical preservatives that can be formulated into the cosmetic compositions of the present invention include amyl gallate, butylated hydroxyanisole (BHA), butylated hydroxytoluene (BHT), 2,5-di-tertbutyl hydroquinone, norhydroquaiaretic acid, butyl p-hydroxybenzoate, dihydroxybenzoate (methyl paraben), propyl gallate, propyl-p-hydroxybenzoate, hydroxychromans, hydroxycoumarans, tocopherols, solvent extracted wheat germ oil, casein, edestin, ethanolamine, glutamic acid, hydroxamic acids, kephalin, lecithin, plant and animal phosphatides, purines (xanthine and uric acid), ascorbin acid, citric acid, dilauryl thiopropionate, distearyl thiopropionate, galactaronic acid, glucurronic acid, isopropyl citrate, maleic acid, malonic acid, mannitol, oxalic acid, propionic acid, sorbitol, tartaric acid, thiopropionic acid, phosphoric acid and its salts and phosphorous acid and its salts. Any of the above preservatives can be used, as long as it is compatible with the other components of the cosmetic stick formulation. The preservative is present in an amount effective to impart preservation. Typical amounts of preservative are from 0.05 to 0.2 weight percent.

The cosmetic compositions of the present invention preferably include a fragrance, however, they also can be manufactured unscented. Total fragrance levels of the present invention may vary from 0.5 to 5 weight percent of the composition. Preferably, total fragrance will be from 0.8 to 3 weight percent, more preferably from 1 to 2 weight percent.

Any type of fragrance may be used in the compositions of the present invention. These fragrances include natural oils, synthetic components, or mixtures thereof.

Other miscellaneous ingredients of the cosmetic sticks of the present invention include herbal materials, colorings, and dyes.

The invention also provides a process for preparing a transparent cosmetic composition of the invention. The process comprises combining the ingredients in liquid form. To manufacture a stick, the combined ingredients are poured into a container having a particular shape so that the solid which forms takes the shape of the container.

A preferred embodiment of the invention is in the form of a stick of circular or oval cross-section contained in a stick dispenser or holder. Suitable dispensers or holders have an airtight cap so as to prevent evaporation of volatile ingredients during storage between uses.

The cosmetic compositions of the invention are applied to the hair as desired to impart either, holding, shining or conditioning properties to the hair. The stick is typically rubbed on the hair to leave a deposit of the cosmetic composition. The hair may be either wet or dry.

The following examples are illustrative of the invention, but are not intended to limit the scope of the invention in any way. The parts and percentages in the examples are represented by weight.

Procedure for Making Cosmetic Hair Conditioning Sticks

The sticks are made by the following method. The materials are combined, except for the fragrance and coloring, in a Griffin beaker of appropriate size and heated at a temperature of from about 75 C. to about 90 C. The materials are mixed with moderate agitation until all solid components are melted and the batch is uniform. The solution is then cooled to about 60 C. and the fragrance and coloring are then mixed in. The solution is then poured into a stick mold and allowed to solidify.

Example 1

Example 1 was made by the procedure for making cosmetic hair conditioning sticks described above. The components of the solution are given in the following table. All of the components except the fragrance, methyl paraben, and Germall II were added and dissolved. Then, the fragrance, methyl paraben, and Germall II were added and the procedure described above was followed. GERMALL II is a preservative available from International Specialty Products. PEG-6 Caprylic/capric triglyceride is available from Huls America, Inc. under the tradename Softigen 767. PVP/VA copolymer is available from BASF under the tradename Luviskol.

| COMPONENT | WT % |
| --- | --- |
| Water | 25.6 |
| Sodium Stearate | 7.0 |
| PEG-6 Caprylic/capric triglyceride | 20.0 |
| Sugar | 6.0 |
| Glycerin | 20.0 |
| Methyl paraben | 0.1 |
| PVP/VA copolymer | 10.0 |
| Ethanol | 10.0 |
| Fragrance | 1.0 |
| Germall II | 0.3 |
| TOTAL | 100.0 |

Example 2

Example 2 was made by the procedure of Example 1.

| | |
| --- | --- |
| Water | 26.5 |
| Sodium Stearate | 7.0 |
| PEG-6 Caprylic/capric triglyceride | 36.0 |
| Table sugar | 6.0 |
| Copolymer of vinyl pyrrolidone/vinyl acetate | 10.0 |
| Ethanol | 13.1 |
| Fragrance | 1.0 |
| Methyl paraben | 0.1 |
| Germall II | 0.3 |
| TOTAL | 100.0 |

Example 3

Example 3 is made by the procedure of Example 1.

| | |
| --- | --- |
| Water | 25.6 |
| Sodium Stearate | 7.0 |
| PEG-6 Caprylic/capric triglyceride | 20.0 |
| Sugar | 6.0 |
| Glycerin | 20.0 |
| Propyl paraben | 0.1 |
| Poly (vinyl pyrrolidone/acrylamide) | 10.0 |

| COMPONENT | WT % |
|---|---|
| copolymer | |
| Ethanol | 10.0 |
| Fragrance | 1.0 |
| Germall II | 0.300 |
| TOTAL | 100.000 |

Example 4
Example 4 is made by the procedure of Example 1.

| COMPONENT | WT % |
|---|---|
| Water | 25.6 |
| Sodium Stearate | 7.0 |
| PEG-6 Caprylic/capric triglyceride | 20.0 |
| Sugar | 6.0 |
| Glycerin | 20.0 |
| Methyl paraben | 0.1 |
| Polyvinyl pyrrolidone | 10.0 |
| Ethanol | 10.0 |
| Fragrance | 1.0 |
| Germall II | 0.3 |
| TOTAL | 100.0 |

Example 5
Example 5 is made by the procedure of Example 1

| COMPONENT | WT % |
|---|---|
| Water | 25.6 |
| Sodium Stearate | 7.0 |
| PEG-6 Caprylic/capric triglyceride | 20.0 |
| Sugar | 6.0 |
| Ethylene glycol | 20.0 |
| Methyl paraben | 0.1 |
| Copolymer of vinyl pyrrolidone and vinyl acetate (PVP/VA copolymer) | 10.0 |
| Ethanol | 10.0 |
| Fragrance | 1.0 |
| Germall II | 0.3 |
| TOTAL | 100.0 |

Example 6
Example 6 is made by the procedure of Example 1.

| COMPONENT | WT % |
|---|---|
| Water | 25.6 |
| Sodium Stearate | 7.0 |
| PEG-6 Caprylic/capric triglyceride | 20.0 |
| Sugar | 6.0 |
| Glycerin | 20.0 |
| Propyl paraben | 0.1 |
| Ethyl cellulose | 10.0 |
| Ethanol | 10.0 |
| Fragrance | 1.0 |
| Germall II | 0.3 |
| TOTAL | 100.0 |

Example 7
Example 7 is made by the procedure of Example 1.

| COMPONENT | WT % |
|---|---|
| Water | 25.6 |
| Sodium Stearate | 7.0 |
| PEG-6 Caprylic/capric triglyceride | 20.0 |
| Sugar | 6.0 |
| Glycerin | 20.0 |
| Methyl paraben | 0.1 |
| Vinyl acetate/crotonic acid copolymer | 10.0 |
| Ethanol | 10.0 |
| Fragrance | 1.0 |
| Germall II | 0.3 |
| TOTAL | 100.0 |

Example 8
Example 8 is made by the procedure of Example 1.

| COMPONENT | WT % |
|---|---|
| Water | 25.6 |
| Sodium Stearate | 7.0 |
| PEG-6 Caprylic/capric triglyceride | 20.0 |
| Sugar | 6.0 |
| Ethylene glycol | 20.0 |
| Methyl paraben | 0.1 |
| Eastman AQ sulfopolyester polymers | 10.0 |
| Ethanol | 10.0 |
| Fragrance | 1.0 |
| Germall II | 0.3 |
| TOTAL | 100.0 |

Example 9
Example 9 is made by the procedure of Example 1.

| COMPONENT | WT % |
|---|---|
| Water | 25.6 |
| Sodium Stearate | 7.0 |
| PEG-6 Caprylic/capric triglyceride | 20.0 |
| Sugar | 6.0 |
| Glycerin | 20.0 |
| Methyl paraben | 0.1 |
| Vinyl pyrrolidone/ethyl methacrylate copolymer | 10.0 |
| Ethanol | 10.0 |
| Fragrance | 1.0 |
| Germall II | 0.3 |
| TOTAL | 100.0 |

Example 10
Example 10 is made by the procedure of Example 1.

| COMPONENT | WT % |
|---|---|
| Water | 25.6 |
| Sodium Stearate | 7.0 |
| PEG-6 Caprylic/capric triglyceride | 20.0 |
| Sugar | 6.0 |
| Glycerin | 20.0 |
| Methyl paraben | 0.1 |
| Copolymer of Dimethyldiallylammonium chloride and hydroxyethylcellulose | 10.0 |
| Ethanol | 10.0 |
| Fragrance | 1.0 |
| Germall II | 0.3 |
| TOTAL | 100.0 |

Example 11
Example 11 is made by the procedure of Example 1.

| COMPONENT | WT % |
|---|---|
| Water | 20.6 |
| Sodium Stearate | 7.0 |
| PEG-6 Caprylic/capric triglyceride | 20.0 |
| Sugar | 6.0 |
| Ethylene glycol | 25.0 |
| Methyl paraben | 0.1 |
| Hydroxypropyl cellulose | 10.0 |
| Ethanol | 10.0 |
| Fragrance | 1.0 |
| Germall II | 0.3 |
| TOTAL | 100.0 |

Example 12
Example 12 is made by the procedure of Example 1.

| COMPONENT | WT % |
|---|---|
| Water | 25.6 |
| Sodium Stearate | 7.0 |
| PEG-6 Caprylic/capric triglyceride | 20.0 |
| Sugar | 6.0 |

| COMPONENT | WT % |
|---|---|
| Glycerin | 20.0 |
| Methyl paraben | 0.1 |
| Chitosan | 10.0 |
| Ethanol | 10.0 |
| Fragrance | 1.0 |
| Germall II | 0.3 |
| TOTAL | 100.0 |

Example 13
Example 13 is made by the procedure of Example 1.

| COMPONENT | WT % |
|---|---|
| Water | 25.6 |
| Sodium Stearate | 7.0 |
| PEG-6 Caprylic/capric triglyceride | 20.0 |
| Sugar | 6.0 |
| Glycerin | 20.0 |
| Methyl paraben | 0.1 |
| Vinylpyrrolidone/Dimethylaminoethyl methacrylate copolymer | 10.0 |
| Ethanol | 10.0 |
| Fragrance | 1.0 |
| Germall II | 0.3 |
| TOTAL | 100.0 |

Example 14
Example 14 is made by the procedure of Example 1.

| COMPONENT | WT % |
|---|---|
| Water | 25.6 |
| Sodium Stearate | 7.0 |
| PEG-6 Caprylic/capric triglyceride | 20.0 |
| Sugar | 6.0 |
| Glycerin | 20.0 |
| Methyl paraben | 0.1 |
| Vinyl caprolactam/vinylpyrrolidone copolymer | 10.0 |
| Ethanol | 10.0 |
| Fragrance | 1.0 |
| Germall II | 0.3 |
| TOTAL | 100.0 |

Example 15
Example 15 is made by the procedure of Example 1.

| COMPONENT | WT % |
|---|---|
| Water | 30.0 |
| Sodium Stearate | 7.0 |
| Vinyl pyrrolidone/vinyl acetate copolymer | 10.0 |
| Ethanol | 10.0 |
| Isopropyl Alcohol | 6.6 |
| PRG-B Caprylic/capric triglyceride | 35.0 |
| Methyl paraben | 0.1 |
| Fragrance | 1.0 |
| Germall II | 0.3 |
| TOTAL | 100.0 |

Example 16
Example 16 is made by the procedure of Example 1.

| COMPONENT | WT % |
|---|---|
| Water | 25.1 |
| Propylene glycol | 50.0 |
| Vinyl pyrrolidone/vinyl acetate copolymer | 10.0 |
| Sodium stearate | 7.5 |
| Ethanol | 6.0 |
| Fragrance | 1.0 |
| Propyl paraben | 0.1 |
| Germall II | 0.3 |
| TOTAL | 100.0 |

Example 17
Example 17 is made by the procedure of Example 1.

| COMPONENT | WT % |
|---|---|
| Water | 25.6 |
| Sodium Stearate | 7.0 |
| PEG-6 Caprylic/capric triglyceride | 20.0 |
| Table sugar | 6.0 |
| Glycerin | 20.0 |
| Methyl paraben | 0.1 |
| Vinyl alcohol/vinyl acetate copolymer | 10.0 |
| Ethanol | 10.0 |
| Fragrance | 1.0 |
| Germall II | 0.3 |
| TOTAL | 100.0 |

Example 18
Example 18 is made by the procedure of Example 1.

| COMPONENT | WT % |
|---|---|
| Water | 26.0 |
| Sodium Stearate | 7.0 |
| PEG-6 Caprylic/capric triglyceride | 36.0 |
| Table sugar | 6.0 |
| Polyvinyl pyrrolidone | 11.1 |
| Ethanol | 12.5 |
| Fragrance | 1.0 |
| Methyl paraben | 0.1 |
| Germall II | 0.3 |
| TOTAL | 100.0 |

Example 19
Example 19 is made by the procedure of Example 1.

| COMPONENT | WT % |
|---|---|
| Water | 26.6 |
| Sodium Stearate | 7.0 |
| PEG-6 Caprylic/capric triglyceride | 36.0 |
| Table sugar | 6.5 |
| Polyacrylic acid | 10.0 |
| Ethanol | 12.5 |
| Fragrance | 1.0 |
| Methyl paraben | 0.1 |
| Germall II | 0.3 |
| TOTAL | 100.0 |

Example 20
Example 20 is made by the procedure of Example 1.

| COMPONENT | WT % |
|---|---|
| Water | 26.0 |
| Sodium Stearate | 7.0 |
| PEG-6 Caprylic/capric triglyceride | 36.0 |
| Table sugar | 6.0 |
| Polyquaternium 4-copolymer of hydroxyethyl cellulose and diallyl dimethylammonium chloride | 11.1 |
| Ethanol | 12.5 |
| Fragrance | 1.0 |
| Methyl paraben | 0.1 |
| Germall II | 0.3 |
| TOTAL | 100.0 |

Example 21
Example 21 is made by the procedure of Example 1.

| COMPONENT | WT % |
|---|---|
| Water | 27.6 |
| Sodium Stearate | 7.5 |
| PEG-6 Caprylic/capric triglyceride | 36.0 |
| Table sugar | 6.0 |
| Poly(ethylhexyl methacrylate) | 10.0 |
| Ethanol | 12.5 |
| Methyl paraben | 0.1 |
| Germall II | 0.3 |
| TOTAL | 100.0 |

| COMPONENT | WT % |
|---|---|
| Example 22 | |
| *Example 22 is made by the procedure of Example 1.* | |
| Water | 26.0 |
| Sodium Stearate | 7.0 |
| PEG-6 Caprylic/capric triglyceride | 36.0 |
| Table sugar | 6.0 |
| Polydiallyldimethyl ammonium chloride | 11.1 |
| Ethanol | 12.5 |
| Fragrance | 1.0 |
| Methyl paraben | 0.1 |
| Germall II | 0.3 |
| TOTAL | 100.0 |
| Example 23 | |
| *Example 23 is made by the procedure of Example 1.* | |
| Water | 26.0 |
| Sodium Stearate | 7.0 |
| PEG-6 Caprylic/capric triglyceride | 36.0 |
| Table sugar | 6.0 |
| Hydroxyethylcellulose | 11.1 |
| Ethanol | 12.5 |
| Fragrance | 1.0 |
| Methyl paraben | 0.1 |
| Germall II | 0.3 |
| TOTAL | 100.0 |
| Example 24 | |
| *Example 24 is made by the procedure of Example 1.* | |
| Water | 26.0 |
| Sodium Stearate | 7.0 |
| PEG-6 Caprylic/capric triglyceride | 36.0 |
| Table sugar | 6.0 |
| Chitosan | 11.1 |
| Ethanol | 12.5 |
| Fragrance | 1.0 |
| Methyl paraben | 0.1 |
| Germall II | 0.3 |
| TOTAL | 100.0 |
| Example 25 | |
| *Example 25 is made by the procedure of Example 1.* | |
| Water | 26.0 |
| Sodium Stearate | 7.0 |
| PEG-6 Caprylic/capric triglyceride | 36.0 |
| Table sugar | 6.0 |
| Copolymer of vinylpyrrolidone/dimethylamino ethyl methacrylate quaternized with diethyl sulfate | 11.1 |
| Ethanol | 12.5 |
| Fragrance | 1.0 |
| Methyl paraben | 0.1 |
| Germall II | 0.3 |
| TOTAL | 100.0 |
| Example 26 | |
| *Example 26 is made by the procedure of Example 1.* | |
| Water | 26.6 |
| Sodium Stearate | 7.0 |
| PEG-6 Caprylic/capric triglyceride | 36.5 |
| Table sugar | 6.0 |
| Polysilane 2-polymer formed by the reaction of tetradecene with polymerized tetramethyl cyclosiloxane | 10.0 |
| Ethanol | 12.5 |
| Fragrance | 1.0 |
| Methyl paraben | 0.1 |
| Germall II | 0.3 |
| TOTAL | 100.0 |
| Example 27 | |
| *Example 27 is made by the procedure of Example 1.* | |
| Water | 26.5 |
| Sodium Stearate | 7.1 |
| PEG-6 Caprylic/capric triglyceride | 36.0 |
| Table sugar | 6.5 |
| Vinyl acetate/crotonic acid copolymer | 10.0 |
| Ethanol | 12.5 |
| Fragrance | 1.0 |
| Methyl paraben | 0.1 |
| Germall II | 0.3 |
| TOTAL | 100.0 |
| Example 28 | |
| *Example 28 is made by the procedure of Example 1.* | |
| Water | 26.5 |
| Sodium Stearate | 7.1 |
| PEG-6 Caprylic/capric triglyceride | 36.4 |
| Table sugar | 6.1 |
| Copolymer of vinyl pyrrolidone/vinyl acetate | 10.0 |
| Ethanol | 12.5 |
| Fragrance | 1.0 |
| Methyl paraben | 0.1 |
| Germall II | 0.3 |
| TOTAL | 100.0 |
| Example 29 | |
| *Example 29 is made by the procedure of Example 1.* | |
| Water | 20.0 |
| Propylene glycol | 50.0 |
| Sodium stearate | 7.0 |
| Polyacrylic acid | 10.0 |
| Fragrance | 1.0 |
| Methyl paraben | 0.1 |
| Ethanol | 12.9 |
| TOTAL | 100.0 |
| Example 30 | |
| *Example 30 is made by the procedure of Example 1.* | |
| Water | 20.0 |
| Propylene glycol | 55.0 |
| Sodium stearate | 7.5 |
| Chitosan | 10.0 |
| Fragrance | 1.0 |
| Methyl paraben | 0.1 |
| Ethanol | 6.4 |
| TOTAL | 100.0 |
| Example 31 | |
| *Example 31 is made by the procedure of Example 1.* | |
| Water | 20.0 |
| Propylene glycol | 55.0 |
| Sodium stearate | 7.5 |
| Polyvinyl pyrrolidone | 10.0 |
| Fragrance | 1.0 |
| Methyl paraben | 0.1 |
| Ethanol | 6.4 |
| TOTAL | 100.0 |

| COMPONENT | WT % |
|---|---|
| Example 32 | |
| *Example 32 is made by the procedure of Example 1.* | |
| Reaction product of butyl alcohol with 14 moles of propylene oxide | 55.0 |
| Propylene glycol | 20.0 |
| Sodium stearate | 7.5 |
| Vinyl acetate/vinyl pyrrolidone copolymer | 10.0 |
| Fragrance | 1.0 |
| Methyl paraben | 0.1 |
| Ethanol | 6.4 |
| TOTAL | 100.0 |
| Example 33 | |
| *Example 33 is made by the procedure of Example 1.* | |
| Reaction product of myristyl alcohol with 3 moles of propylene oxide | 20.0 |
| Propylene glycol | 18.5 |
| Sodium stearate | 7.5 |
| Polyethylmethacrylate | 10.0 |
| Fragrance | 1.0 |
| Methyl paraben | 0.1 |
| Ethanol | 6.4 |
| TOTAL | 100.0 |
| Example 34 | |
| *Example 34 is made by the procedure of Example 1.* | |
| PPG-3 Myristyl ether | 28.0 |
| Propylene glycol | 12.0 |
| Cyclomethicone | 34.9 |
| Sodium Stearate | 6.0 |
| Polyethylmethacrylate | 10.0 |
| Fragrance | 1.0 |
| Methyl paraben | 0.1 |
| Ethanol | 8.0 |
| TOTAL | 100.0 |
| Example 35 | |
| *Example 35 is made by the procedure of Example 1.* | |
| PPG-10 Cetyl ether | 18.0 |
| Propylene glycol | 22.0 |
| Cyclomethicone | 34.9 |
| Sodium Stearate | 6.0 |
| PVP/VA | 10.0 |
| Fragrance | 1.0 |
| Propyl paraben | 0.1 |
| Ethanol | 8.0 |
| TOTAL | 100.0 |
| Example 36 | |
| *Example 36 is made by the procedure of Example 1.* | |
| Cetyl alcohol | 19.9 |
| Propylene glycol | 20.0 |
| Dimethylcyclosiloxane | 35.0 |
| Sodium Stearate | 6.0 |
| PVP/VA | 10.0 |
| Fragrance | 1.0 |
| Propyl paraben | 0.1 |
| Ethanol | 8.0 |
| TOTAL | 100.0 |
| Example 37 | |
| *Example 37 is made by the procedure of Example 1.* | |
| Stearyl alcohol | 19.9 |
| Propylene glycol | 10.0 |
| Dimethylcyclosiloxane | 45.0 |
| Sodium Stearate | 6.9 |
| Polyvinyl acetate | 10.0 |
| Fragrance | 1.0 |
| Propyl paraben | 0.1 |
| Ethanol | 8.0 |
| TOTAL | 100.0 |

The above description is provided for the purpose of describing embodiments of the invention and are not intended to limit the scope of the invention in any way. It will be apparent to those skilled in the art that various modifications and variations can be made in the cosmetic hair conditioning solid and device and their uses without departing from the spirit or scope of the invention. Thus, it is intended that the present invention cover the modifications and variations of this invention provided they come within the scope of the appended claims and their equivalents.

What is claimed is:

1. A cosmetic hair conditioning composition comprising an effective amount of a film-forming polymer solubilized in an alcohol and/or water-containing cosmetically acceptable vehicle gelled by a fatty acid soap; wherein the film-forming polymer is a synthetic polymer or copolymer polymerized from an ethylenically unsaturated monomer or mixtures thereof, the monomer being selected from the group consisting of vinyl alcohol, vinyl acetate, vinyl propionate, N-vinyl acetamide, N-vinyl pyrrolidone, N-vinyl caprolactam, acrylic acid, methacrylic acid, C1–C12 esters of acrylic and methacrylic acid, acrylamide, methacrylamide, crotonic acid, vinyl neodecanoate, styrene, vinyl laurate, N-tertiary butyl acrylamide, methyl vinyl ether, ethylene, monobutyl maleate, maleic anhydride, allyl acetate, isobutyl vinyl ether, N,N-dimethylaminoethyl (meth)acrylate and its derivatives quaternized with dimethyl and diethyl sulfate, diallyl dimethyl ammonium chloride, vinyl substituted siloxanes and mixtures thereof; or a naturally occurring polymer or copolymer selected from the group consisting of cellulose, modified cellulose, carbohydrate polymer, and a modified carbohydrate polymer; and wherein the composition is in the form of a solid stick.

2. The cosmetic hair conditioning composition of claim 1, wherein the composition has a minimum hardness such that it will have a penetration measurement of not more than 200 in the Penetrometer Test.

3. The cosmetic hair conditioning composition of claim 1, wherein the composition has a minimum hardness such that it will have a penetration measurement of from 50 to 70 in the Penetrometer Test.

4. The cosmetic hair conditioning composition of claim 1, wherein the composition transfers an effective amount of a film forming polymer to hair when applied by hand.

5. The cosmetic hair conditioning composition of claim 1, wherein the composition is in the form of a cylinder.

6. The cosmetic hair conditioning composition of claim 1, wherein the film forming polymer is present in an amount of from 1 to 40 percent by weight.

7. The cosmetic hair conditioning composition of claim 1, wherein the film forming polymer is present in an amount of from 1 to 20 percent by weight.

8. The cosmetic hair conditioning composition of claim 1, wherein the film forming polymer is present in an amount of from 3 to 15 percent by weight.

9. The cosmetic hair conditioning composition of claim 1, wherein the film forming polymer is a synthetic polymer or copolymer.

10. The cosmetic hair conditioning composition of claim 1, wherein the film forming polymer is a naturally occurring polymer or copolymer.

11. The cosmetic hair conditioning composition of claim 1, wherein the composition comprises at least one film forming polymer that is a synthetic polymer or copolymer and at least one film forming polymer that is a naturally occurring polymer or copolymer.

12. The cosmetic hair conditioning composition of claim 1, wherein the cosmetically acceptable vehicle is an aqueous vehicle.

13. The cosmetic hair conditioning composition of claim 1, wherein the cosmetically acceptable vehicle is a non-aqueous vehicle.

14. The cosmetic hair conditioning composition of claim 9, wherein the synthetic polymer or copolymer is polymerized from an ethylenically unsaturated monomer or mixtures thereof.

15. The cosmetic hair conditioning composition of claim 10, wherein the naturally occurring polymer or copolymer is cellulose, modified cellulose, carbohydrate polymer, or a modified carbohydrate polymer.

16. The cosmetic hair conditioning composition of claim 1, wherein the film forming polymer is selected from vinyl acetate/vinyl pyrrolidone copolymer, vinyl alcohol/vinyl acetate copolymer, vinyl pyrrolidone/acrylamide copolymer, ethyl cellulose, vinyl acetate/crotonic acid copolymer, sulfopolyester polymers, vinyl pyrrolidone/ethyl methacrylate copolymer, copolymer of dimethyl diallyl ammonium chloride and hydroxyethyl cellulose, hydroxypropyl cellulose, chitosan, vinylpyrrolidone/dimethylaminoethyl methacrylate copolymer, vinyl caprolactam/vinyl pyrrolidone copolymer, polyvinylpyrrolidone, polyacrylic acid, polyquaternium 4-copolymer of hydroxyethyl cellulose and diallyldimethyl ammonium chloride, poly(ethylhexyl methacrylate), polydiallyldimethyl ammonium chloride, hydroxyethylcellulose, copolymer of vinylpyrrolidone/ dimethylamino ethyl methacrylate quaternized with diethyl sulfate, polysilane 2-polymer formed by the reaction of tetradecene with polymerized tetramethyl cyclosiloxane, polyethylmethacrylate, or polyvinylacetate.

17. The cosmetic hair conditioning composition of claim 1, wherein the film forming polymer is a vinyl acetate/vinyl pyrrolidone copolymer.

18. The cosmetic hair conditioning composition of claim 1, wherein the cosmetically acceptable vehicle comprises:
    (a) a fatty acid soap;
    (b) a nonionic component; and
    (c) water.

19. The cosmetic hair conditioning composition of claim 1, wherein the cosmetically acceptable vehicle comprises:
    (a) a fatty acid soap;
    (b) a nonionic component; and
    (c) a lower alcohol.

20. The cosmetic hair conditioning composition of claim 1, wherein the composition comprises:
    (a) 1 to 15 weight percent of the film forming polymer;
    (b) 3 to 10 weight percent of a fatty acid soap;
    (c) 0 to 60 weight percent of a polyhydric alcohol;
    (d) 15 to 60 weight percent of a nonionic component; and
    (e) 10 to 50 weight percent of water, a lower alcohol, or mixtures thereof.

21. The cosmetic hair conditioning composition of claim 21, wherein the composition comprises:
    (a) 3 to 10 weight percent of the film forming polymer;
    (b) 3 to 10 weight percent of a fatty acid soap;
    (c) 15 to 40 weight percent of a polyhydric alcohol;
    (d) 25 to 40 weight percent of a nonionic component; and
    (e) 20 to 45 weight percent of water, a lower alcohol, or mixtures thereof.

22. The cosmetic hair conditioning composition of claim 1, wherein the composition comprises a sugar.

23. The cosmetic hair conditioning composition of claim 1, wherein the composition comprises table sugar.

24. The cosmetic hair conditioning composition of claim 1, wherein the composition comprises a polyhydric alcohol.

25. The cosmetic hair conditioning composition of claim 1, wherein the composition comprises a polyhydric alcohol selected from ethylene glycol, propylene glycol, or glycerol.

26. The cosmetic hair conditioning composition of claim 1, wherein the composition comprises sodium stearate.

27. The cosmetic hair conditioning composition of claim 1, wherein the composition is transparent.

28. The cosmetic hair conditioning composition of claim 1, wherein the composition is translucent.

29. The cosmetic hair conditioning composition of claim 1, wherein the cosmetically acceptable vehicle comprises:
    (a) a polyhydric alcohol;
    (b) a $C_{14}$–$C_{18}$ sodium or potassium fatty acid soap;
    (c) a PEG-6 caprylic/capric triglyceride;
    (d) water;
    (e) a sugar; and
    (f) a $C_2$–$C_3$ monohydroxy alcohol.

30. The cosmetic hair conditioning composition of claim 1, wherein the cosmetically acceptable vehicle is nonaqueous and comprises:
    (a) a polyhydric alcohol;
    (b) a $C_{14}$–$C_{18}$ sodium or potassium fatty acid soap; and
    (c) an alkoxylate copolymer.

31. The cosmetic hair conditioning composition of claim 30, wherein the alkoxylate copolymer is a product having the formula

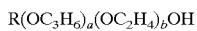

wherein R is selected from hydrogen or hydrocarbon chains having from 2 to 20 carbon atoms, a and b are each from 0 to 35 and the sum of a+b is from 5 to 35.

32. A cosmetic hair conditioning composition of claim 1 comprising:
    (a) 5 to 30 weight percent water;
    (b) 0 to 60 weight percent of an aliphatic polyhydric alcohol having from 2 to 3 carbon atoms and from 2 to 3 hydroxyl groups;
    (c) 20 to 50 weight percent of a nonionic compound selected from $C_{12}$–$C_{18}$ alcohol alkoxylates, PEG (1–10) caprylic/capric triglycerides, or mixtures thereof;
    (d) 1 to 10 weight percent of a film forming polymer;
    (e) 3 to 7 weight percent of a sugar;
    (f) 3 to 10 weight percent of a fatty acid soap; and
    (g) 10 to 15 weight percent of an alcohol selected from ethanol, isopropyl alcohol or mixtures thereof;
    wherein the composition is in the form of a solid.

33. The cosmetic hair conditioning composition of claim 32, wherein the polyhydric alcohol is selected from ethylene glycol, propylene glycol, or glycerol.

34. The cosmetic hair conditioning composition of claim 32, wherein the nonionic material is PEG-6 caprylic/capric triglyceride.

35. The cosmetic hair conditioning composition of claim 32, wherein the film forming polymer is a polymer or copolymer polymerized from an ethylenically unsaturated monomer selected from vinyl alcohol, vinyl acetate, vinyl propionate, N-vinyl acetamide, N-vinyl pyrrolidone, N-vinyl caprolactam, acrylic acid, methacrylic acid, $C_1$–$C_{12}$ esters of acrylic and methacrylic acid, acrylamide, methacrylamide, crotonic acid, vinyl neodecanoate, styrene, vinyl laurate, N-tertiary butyl acrylamide, methyl vinyl ether, ethylene, monobutyl maleate, maleic anhydride, allyl acetate, isobutyl vinyl ether, N,N-dimethylaminoethyl (meth) acrylate and its derivatives quaternized with dimethyl and diethyl sulfate, diallyl dimethyl ammonium chloride, vinyl substituted siloxanes or mixtures thereof.

36. The cosmetic hair conditioning composition of claim 32, wherein the film forming polymer is cellulose, modified cellulose, carbohydrate polymer, or a modified carbohydrate polymer.

37. The cosmetic hair conditioning composition of claim 32, wherein the film forming polymer is selected from methyl cellulose, ethyl cellulose, hydroxyethyl cellulose, propylcellulose, hydroxypropylcellulose, carboxymethyl cellulose, chitosan, hydroxymethylcellulose, carboxyethyl cellulose, xanthan gum, alginic acid, quaternary nitrogen-containing cellulose ethers, graft copolymers of N,N-diallyl dimethyl ammonium chloride with cellulose, hydroxyethylcellulose and galactomannan gums, or quaternary chitosan derivatives, and modified forms thereof.

38. The cosmetic hair conditioning composition of claim 32, wherein the film forming polymer is a vinyl acetate/vinyl pyrrolidone copolymer.

39. The cosmetic hair conditioning composition of claim 32, wherein the sugar is table sugar.

40. The cosmetic hair conditioning composition of claim 38, wherein the fatty acid soap is sodium stearate.

41. A method of conditioning hair comprising applying a cosmetic hair conditioning composition to hair so that it is conditioned, wherein the cosmetic hair conditioning composition comprises an effective amount of a film-forming polymer solublized in an alcohol and/or water-containing cosmetically acceptable vehicle gelled by a fatty acid soap; wherein the film-forming polymer is a synthetic polymer or copolymer polymerized from an ethylenically unsaturated monomer or mixtures thereof, the monomer being selected from the group consisting of vinyl alcohol, vinyl acetate, vinyl propionate, N-vinyl acetamide, N-vinyl pyrrolidone, N-vinyl caprolactam, acrylic acid, methacrylic acid, C1–C12 esters of acrylic and methacrylic acid, acrylamide, methacrylamide, crotonic acids vinyl neodecanoate, styrene, vinyl laurate, N-tertiary butyl acrylamide, methyl vinyl ether, ethylene, monobutyl maleate, maleic anhydride, allyl acetate, isobutyl vinyl ether, N,N-dimethylaminoethyl (meth)acrylate and its derivatives quaternized with dimethyl and diethyl sulfate diallyl dimethyl ammonium chloride, vinyl substituted siloxanes and mixtures thereof; or a naturally occurring polymer or copolymer selected from the group consisting of cellulose, modified cellulose, carbohydrate polymer, and a modified carbohydrate polymer; and wherein the composition is in the form of a solid stick.

42. The method of claim 41, wherein the cosmetic hair conditioning composition is applied by hand.

43. The method of claim 41, wherein the cosmetic hair conditioning composition is applied to hair that is wet.

44. A method of styling hair comprising applying a cosmetic hair conditioning composition to hair so that it is styled, wherein the cosmetic hair conditioning composition comprises:

(i) an effective amount of a film forming polymer solubilized in an alcohol and/or water-containing cosmetically acceptable vehicle gelled by a fatty acid soap; wherein the film-forming polymer is a synthetic polymer or copolymer polymerized from an ethylenically unsaturated monomer or mixtures thereof, the monomer being selected from the group consisting of vinyl alcohol, vinyl acetate, vinyl propionate, N-vinyl acetamide, N-vinyl pyrrolidone, N-vinyl caprolactam, acrylic acid, methacrylic acid, $C_1$–$C_{12}$ esters of acrylic and methacrylic acid, acrylamide, methacrylamide, crotonic acid, vinyl neodecanoate, styrene, vinyl laurate, N-tertiary butyl acrylamide, methyl vinyl ether, ethylene, monobutyl maleate, maleic anhydride, allyl acetate, isobutyl vinyl ether, N,N-dimethylaminoethyl (meth) acrylate and its derivatives quaternized with dimethyl and diethyl sulfate, diallyl dimethyl ammonium chloride, vinyl substituted siloxanes and mixtures thereof; or a naturally occurring polymer or copolymer selected from the group consisting of cellulose, modified cellulose, carbohydrate polymer, and a modified carbohydrate polymer; and wherein the composition is in the form of a solid stick.

45. The method of claim 44, wherein the cosmetic hair conditioning composition is applied by hand.

46. The method of claim 44, wherein the cosmetic hair conditioning composition is applied to hair that is dry.

47. The method of claim 44, wherein the cosmetic hair conditioning composition is applied to hair that is slightly wet.

* * * * *